US00PP32109P2

(12) United States Plant Patent
Carruth

(10) Patent No.: US PP32,109 P2
(45) Date of Patent: Aug. 25, 2020

(54) FLORIBUNDA ROSE PLANT NAMED 'WEKLOVAPKEMU'

(50) Latin Name: *Rosa hybrida*
Varietal Denomination: WEKlovapkemu

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 16/602,711

(22) Filed: Nov. 25, 2019

(51) Int. Cl.
*A01H 5/02* (2018.01)
*A01H 6/74* (2018.01)

(52) U.S. Cl.
USPC ..... Plt./143

(58) Field of Classification Search
USPC ..... Plt./101, 141, 143
See application file for complete search history.

(56) References Cited

U.S. PATENT DOCUMENTS

PP14,731 P3 4/2004 Twomey et al.
PP19,571 P2 12/2008 Zary
PP23,289 P2 1/2013 Bédard

*Primary Examiner* — Susan McCormick Ewoldt
(74) *Attorney, Agent, or Firm* — McKee, Voorhees & Sease, PLC

(57) ABSTRACT

A new variety of Floribunda rose suitable for garden decoration, having flowers of brilliant orange with yellow reverse coloration.

1 Drawing Sheet

Classification: The present invention relates to a new *Rosa hybrida* plant.

Variety denomination: The new plant has the varietal denomination 'WEKlovapkemu'.

BACKGROUND OF THE INVENTION

This invention relates to a new and distinct variety of Floribunda Rose. It has as its seed parent the variety known as 'BAIpeace' (U.S. Plant Pat. No. 14,731) and as its pollen parent the variety known as 'WEKzazette' (U.S. Plant Pat. No. 23,289).

SUMMARY OF THE INVENTION

Among the features which distinguish the new variety from other presently available and commercial rose cultivars known to the inventor are the following combinations of characteristics: its unique brilliant orange with yellow reverse flower coloration, its excellent color stability throughout the life of the flower and its abundant bloom. The plant has a bushy upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKlovapkemu' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'BAIpeace' by the following combination of characteristics:

whereas 'WEKlovapkemu' bears double flowers (about 24 to 32 petals) of brilliant orange with yellow reverse coloration, 'BAIpeace' bears double flowers of blended yellow and carmine pink coloration with significantly heavier petalage (about 40 petals). The new variety is classified as a floribunda rose and bears medium sized flowers (about 6.5 to about 10.4 cm. in diameter), whereas the seed parent is classified as a hybrid tea rose and bears significantly larger flowers (about 13.0 cm. in diameter).

The new variety may be distinguished from its pollen parent, 'WEKzazette' by the following combination of characteristics: whereas 'WEKlovapkemu' bears double flowers (about 24 to 32 petals) of brilliant orange with yellow reverse coloration, 'WEKzazette' bears double flowers of ketchup red and mustard yellow bicolor coloration with lesser petalage (about 20 to 28 petals). The new variety has a bushy upright moderately spreading growing habit (about 108 to about 132 cm. spread at the widest point), whereas the pollen parent has a bushy upright significantly narrower growing habit (about 75 to about 90 cm. spread at the widest point).

COMPARISON WITH THE CLOSEST COMMERCIALLY AVAILABLE CULTIVAR

The new variety may be distinguished from its closest commercially available cultivar, 'JACfrain' (U.S. Plant Pat. No. 19,571) by the following combination of characteristics: whereas 'WEKlovapkemu' bears double flowers (about 24 to 32 petals) with a slight tea fragrance, 'JACfrain' bears double flowers with lesser petalage (about 20 to 25 petals) and with a sweet musk fragrance. The new variety has a bushy upright moderately spreading growing habit (about 108 to about 132 cm. spread at the widest point), whereas the closest commercially available cultivar has an upright significantly narrower growing habit (about 80 cm. spread at the widest point).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly, sometimes in clusters of two to five per stem. Flowers may be borne in regular rounded clusters on strong short to medium length stems (about 15 to about 58 cm.). The cluster ranges from about 12.2 to about 13.7 cm. in diameter. Outdoors, the plant blooms abundantly and nearly continuously during the growing season. The flowers have a slight tea fragrance.

BUD

The peduncle is about 2.4 to about 5.7 cm. in length, of average caliper (about 0.2 to about 0.4 cm. in diameter), and usually erect. It is moderately rough, with some stipitate glands and few hairs. Peduncle color is between 144A and 146B sometimes moderately suffused, especially on the side exposed to the sun, with between 187B and 183B.

Before the calyx breaks, the bud is about 1.0 to about 1.7 cm. in diameter at the widest point, about 1.6 to about 2.1 cm. in length, and pointed to somewhat ovoid in shape. The surface of the bud bears between 7 to 11 foliaceous appendages with some stipitate glands, usually with slender entire foliaceous parts extending beyond the tip of the bud about ¼ or more of its length. Bud color is between 137C and 146B sometimes moderately suffused, especially on the side exposed to the sun, with between 187B and 187A.

The sepals are 5 per flower, about 2.2 to about 3.6 cm. in length and about 0.8 to about 1.0 cm. in width at the widest point. The outer surface color of the sepal is between 137C and 146B sometimes moderately suffused, especially on the side exposed to the sun, with between 187B and 187A. The outer surface of the sepal is somewhat rough and bears between 0 to 6 foliaceous appendages with some stipitate glands. The inner surface color of the sepal is near 146B broadly bordered by near 137A. After the sepals open, the inner surface color is sometimes moderately suffused, especially on the area exposed to the sun, with between 187A and 187B. The inner surface of the sepal is covered with fine wooly tomentum; sepal margins are entire and lined with few stipitate glands and hairs. The sepals are moderately permanent, and usually straight in shape with acute apices.

The receptacle of the flower is of somewhat short to medium length (about 0.3 to about 0.6 cm.) and average in caliper (about 0.6 to about 0.8 cm. in diameter). The receptacle is urn-shaped in form. Its surface is smooth with moderately thick fleshy walls. The receptacle color is between 144A and 146B.

As the petals open (after the calyx breaks), the bud is about 1.5 to about 2.6 cm. in diameter at the widest point, about 1.9 to about 3.4 cm. in length, and pointed to somewhat ovoid in form. The color of the under surfaces of the newly opened petals is between 22A and 22C sometimes moderately blushed on the outermost petals with between 53B and 53C to as dark as near 53A. At the point where the petal attaches, there is a moderately large zone of between 11A and 10A. The color of the upper surfaces of the newly opened petals is between 44B and 43A often moderately suffused with near 44A. At the point where the petal attaches, there is a moderately large zone of between 8A and 7C.

BLOOM

When fully open, the bloom ranges from about 6.5 to about 10.4 cm. in diameter. Petalage is double with about 24 to 32 petals and about 1 to 17 petaloids irregularly arranged. When partially open, the bloom form is moderately high centered to cupped, and the petals are moderately loosely spiraled to somewhat cupped with petal edges somewhat reflexed outward. When fully open, the bloom form is more cupped, and the petals are loosely cupped with petal edges moderately reflexed outward.

PETALS

The substance of the petals is moderately heavy and of medium to somewhat thick thickness, with upper surfaces somewhat satiny and under surfaces slightly shiny to matte. The petals are about 3.3 to about 4.8 cm. in length and about 2.4 to about 4.8 cm. in width at the widest point. Petal margins are entire.

The outer petals are somewhat obovate to nearly round in shape with rounded apices.

The inner petals are moderately obovate in shape with rounded apices.

Petaloids are about 0.7 to about 3.3 cm. in length and about 0.4 to about 2.1 cm. in width at the widest point. Petaloids are irregularly shaped moderately oblanceaolate to somewhat obovate with rounded apices.

NEWLY OPENED FLOWER

The under surface color of the outer petals is between 22C and 22D sometimes lightly blushed with between 60B and 60C. At the point where the petal attaches, there is a very large zone of between 11A and 10A. The upper surface color of the outer petals is between 32A and 33B often moderately suffused with between 43A and 46C. At the point where the petal attaches, there is a very large zone of between 13A and 13B.

The under surface color of the intermediate and inner petals is between 22C and 22D. The upper surface color of the intermediate and inner petals is between 32A and 33B.

The under and upper surface colors of the petaloids are similar in coloration to the upper and under surfaces of the intermediate and inner petals.

The general tonality of the newly opened flower is between 32A and 33B.

THREE-DAY-OLD FLOWER

The under surface color of the outer petals is between 19B and 20C sometimes lightly blushed with between 60B and 60C. At the point where the petal attaches, there is a very large zone of between 10B and 8B. The upper surface color of the outer petals is between 44C and 33B often moderately suffused with between 60A and 60B. At the point where the petal attaches, there is a very small large zone of between 8A and 10A.

The under surface color of the intermediate and inner petals is between 19B and 20C. The upper surface color of the intermediate and inner petals is between 44C and 33B often moderately suffused with between 60A and 60B.

The under and upper surface colors of the petaloids are similar in coloration to the upper and under surfaces of the intermediate and inner petals.

The general tonality of the three-thy-old flower is between 44C and 33B often moderately suffused with between 60A and 60B.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 150) and are arranged regularly about the pistils; a few are mixed with petaloids. The filaments are of somewhat short to medium length (about 0.4 to about 1.4 cm.) most with anthers. Filaments are between 13B and 12A in color. The anthers are of medium size for the class and all open approximately at the same time. Anther color when immature is near 22A on the external part and near 8D on the internal part. Anther color at maturity is near 163A on the external part and near 200A on the internal part. Pollen is moderate and between 18B and 16D in color.

FEMALE REPRODUCTIVE ORGANS

Pistils vary in number (average about 120). The styles are moderately even, somewhat long in length (about 0.5 to about 1.0 cm.), moderately thin in caliper, and loosely bunched. Stigma color is between 10B and 11B. Style color is between 145D and 145C often moderately suffused near the top with between 53A and 53B. Ovaries are usually all enclosed in the calyx. The ovaries are of small size and between 158A and 158B in color.

Hips have not been observed on this variety when grown in Pomona, Calif.

FOLIAGE

The compound leaves are usually comprised of three seven leaflets and are borne abundantly. The five-leaflet leaves are about 7.0 to about 15.8 cm. in length and about 4.7 to about 11.0 cm. in width at the widest point, moderately leathery to somewhat crisp in texture on both sides, and glossy in finish on the upper side and somewhat semi-glossy in finish on the under side. The leaves have a pinnate venation pattern. The terminal leaflets are about 3.0 to about 7.9 cm. in length and about 1.6 to about 4.4 cm. in width at the widest point, shaped moderately ovate to somewhat oval with acute apices and rounded bases. Their margins are usually simply serrate.

The upper surface color of the mature leaf is between 139A and 147A. The under surface color of the mature leaf is between 146A and 147B. The under and upper colors of the leaf veins on the mature leaf are similar in coloration to the upper and under surfaces colors of the mature leaf The upper surface color of the young leaf is between 146B and 146C, often heavily suffused with between 187B and 187A. The under surface color of the young leaf is between 146C and 147C, often heavily suffused with between 187B and 187A. The under and upper colors of the leaf veins on the young leaf are similar in coloration to the upper and under surfaces colors of the young leaf.

The rachis is about 4.2 to about 8.8 cm. in length, about 0.1 to about 0.15 cm in width at the widest point, and moderately rough. The upper side is shallowly grooved with few stipitate glands on the edges of the grooves. The under side of the rachis is moderately rough with very few stipitate glands and small prickles. The rachis color is near 146C on the under side and near 137C on the upper side, often moderately suffused on the young leaves with between 187B and 187A.

The stipules are about 0.9 to about 2.0 cm. in length and of medium width (about 0.4 to about 1.0 cm.) with somewhat short to medium length straight points that usually turn out at an angle of more than 45 degrees and sometimes recurve toward the stem. The under and upper surface color of the stipule is between 137C and 137B. The upper and under surfaces of the stipules are smooth in texture.

The petiole is somewhat light to average in caliper and moderately rough. The upper side is shallowly grooved with few stipitate glands on the edges of the grooves. The under side of the petiole is moderately rough with very few stipitate glands and small prickles. The petiole is about 0.4 to about 2.6 cm. in length and about 0.1 to about 0.15 cm in width at the widest point. The petiole color is near 146C on the under side and near 137C on the upper side, often moderately suffused on the young leaves with between 187B and 187A.

The plant displays an average degree of resistance to powdery mildew (*Sphaerotheca pannosa*), downy mildew (*Peronospora sparsa*), and rust (*Phragmidium* sp.) as compared to other commercial varieties grown under comparable conditions in Pomona, Calif. The plant's winter hardiness and drought/heat tolerance are yet to be determined.

GROWTH

The plant has a bushy upright moderately spreading medium height growing habit (about 96 to about 160 cm. in height and about 108 to about 132 cm. spread at the widest point), with full branching. It displays moderately vigorous growth and the canes are of somewhat heavy caliper for the class (about 1.9 to about 3.1 cm. in diameter at the widest point).

The color of the major stems is between 146A and 146B. The major stems are rough in texture and they bear many large prickles that are about 0.9 to about 1.6 cm. in length. The large prickles are almost straight to angled slightly downward with a medium length broad oval base; prickle color is between 177B and 166C. The major stem bears few small prickles of similar shape and coloration.

The color of the branches is between 146B and 146A. The branches are rough in texture and they bear some large prickles which are of similar shape to the large prickles on the major stems. The prickles are about 0.4 to about 0.6 cm. in length. Prickle color is between 152C and 152D. The branches bear few small prickles of similar shape and coloration.

The color of the new shoots is between 146D and 146C sometimes lightly suffused with between 187B and 187C. The new shoots are rough in texture and they bear some large prickles which are of similar size and shape to the large prickles on the branches; prickle color is between 153A and 152D sometimes lightly suffused with between 187C and 187D. The shoots bear few small prickles of similar shape and coloration.

I claim:

1. A new and distinct Floribunda rose plant of the variety substantially as described and illustrated herein.

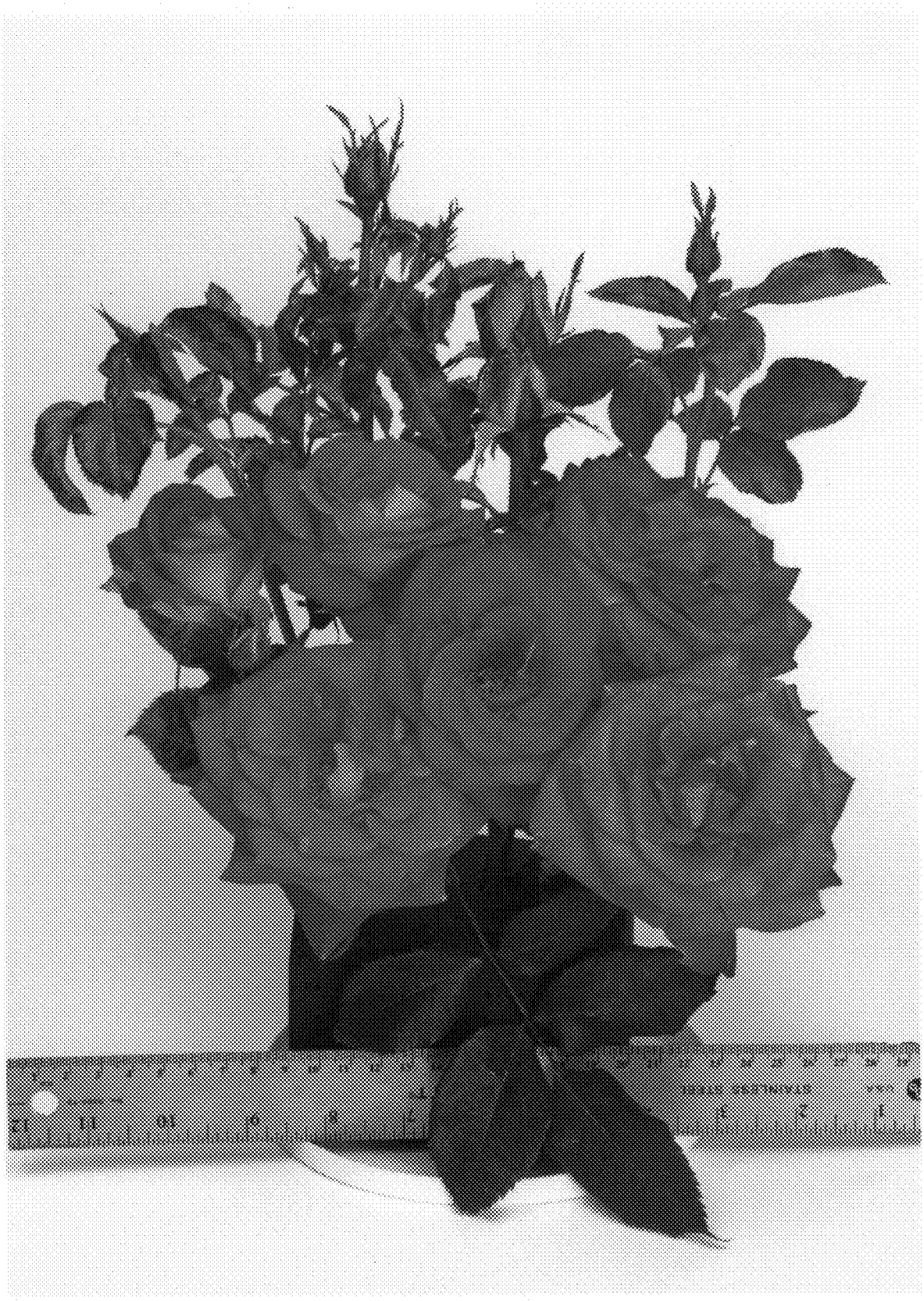

* * * * *